(12) United States Patent
Itai

(10) Patent No.: US 9,542,772 B2
(45) Date of Patent: Jan. 10, 2017

(54) VIRTUAL ENDOSCOPE IMAGE-GENERATING DEVICE, METHOD, AND PROGRAM

(71) Applicant: FUJIFILM Corporation, Tokyo (JP)

(72) Inventor: Yoshinori Itai, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/961,667

(22) Filed: Dec. 7, 2015

(65) Prior Publication Data

US 2016/0086371 A1    Mar. 24, 2016

Related U.S. Application Data

(63) Continuation of application No. PCT/JP2014/003132, filed on Jun. 12, 2014.

(30) Foreign Application Priority Data

Jun. 13, 2013   (JP) .................................. 2013-124350

(51) Int. Cl.
    *G06T 15/08*    (2011.01)
    *A61B 6/03*     (2006.01)
    (Continued)

(52) U.S. Cl.
    CPC ............... *G06T 15/08* (2013.01); *A61B 6/032* (2013.01); *A61B 6/466* (2013.01); *G06T 7/0012* (2013.01);
    (Continued)

(58) Field of Classification Search
    None
    See application file for complete search history.

(56) References Cited

U.S. PATENT DOCUMENTS 5,095,521 A    3/1992 Trousset et al.
5,971,767 A   10/1999 Kaufman et al.
(Continued)

FOREIGN PATENT DOCUMENTS

JP    S63-266583 A    11/1988
JP    2001-502197 A    2/2001
(Continued)

OTHER PUBLICATIONS

International Search Report (ISR) (PCT Form PCT/ISA/210), in PCT/JP2014/003132, dated Oct. 21, 2014.
(Continued)

*Primary Examiner* — Tsung-Yin Tsai
(74) *Attorney, Agent, or Firm* — Mcginn IP Law Group, PLLC

(57) ABSTRACT

A virtual endoscope image is generated based on an opacity template in which a pixel value of a three-dimensional image is associated with an opacity, the opacity template being capable of showing both of an inner wall of a large intestine region and an inner wall of a residue region present in the large intestine region on the virtual endoscope image, a viewpoint set in the vicinity of a boundary between a space region and the residue region in the large intestine region, a set surface set at a position separated by a previously set distance in a previously set line-of-sight direction from the viewpoint, and a pixel value on a light beam vector beyond the set surface among pixel values of the three-dimensional image on the light beam vector extending from the viewpoint.

15 Claims, 5 Drawing Sheets

(51) Int. Cl.
*A61B 6/00* (2006.01)
*G06T 7/00* (2006.01)

(52) U.S. Cl.
CPC ......... *G06T 7/0081* (2013.01); *G06T 2200/04* (2013.01); *G06T 2207/10012* (2013.01); *G06T 2207/10081* (2013.01); *G06T 2207/30004* (2013.01); *G06T 2210/41* (2013.01)

(56) References Cited

U.S. PATENT DOCUMENTS

| | | | |
|---|---|---|---|
| 6,496,188 B1 | 12/2002 | Deschamps et al. | |
| 2001/0031920 A1* | 10/2001 | Kaufman | A61B 5/055 600/431 |
| 2002/0097320 A1* | 7/2002 | Zalis | G06T 5/50 348/65 |
| 2003/0007673 A1* | 1/2003 | Truyen | G06T 19/00 382/128 |
| 2003/0023163 A1* | 1/2003 | Johnson | A61B 6/481 600/431 |
| 2003/0223627 A1* | 12/2003 | Yoshida | G06T 7/0012 382/128 |
| 2005/0054895 A1* | 3/2005 | Hoeg | A61B 90/36 600/117 |
| 2005/0078858 A1* | 4/2005 | Yao | G06K 9/00201 382/128 |
| 2005/0107695 A1* | 5/2005 | Kiraly | G06T 15/06 600/431 |
| 2005/0151732 A1 | 7/2005 | Yamaguchi et al. | |
| 2005/0281381 A1* | 12/2005 | Guendel | G06T 7/0012 378/131 |
| 2005/0281481 A1* | 12/2005 | Guendel | A61B 6/466 382/276 |
| 2006/0276708 A1* | 12/2006 | Peterson | A61B 6/032 600/416 |
| 2007/0276225 A1* | 11/2007 | Kaufman | G06T 7/0012 600/416 |
| 2008/0055308 A1* | 3/2008 | Dekel | G06T 15/08 345/421 |
| 2009/0097728 A1* | 4/2009 | Lee | G06T 7/0081 382/131 |
| 2009/0103793 A1* | 4/2009 | Borland | G06T 15/08 382/131 |
| 2009/0304248 A1 | 12/2009 | Zalis et al. | |
| 2012/0053408 A1* | 3/2012 | Miyamoto | G06T 19/20 600/109 |
| 2012/0136208 A1* | 5/2012 | Itai | G06T 19/003 600/109 |
| 2013/0137926 A1* | 5/2013 | Itai | A61B 1/0005 600/111 |

FOREIGN PATENT DOCUMENTS

| | | |
|---|---|---|
| JP | 2002-534191 A | 10/2002 |
| JP | 2005-182207 A | 7/2005 |
| JP | 2009-511216 A | 3/2009 |
| JP | 2012-504003 A | 2/2012 |
| WO | WO 2010/034968 A1 | 4/2010 |

OTHER PUBLICATIONS

The International Search Opinion (PCT/ISA/237) and an English translation thereof.

* cited by examiner

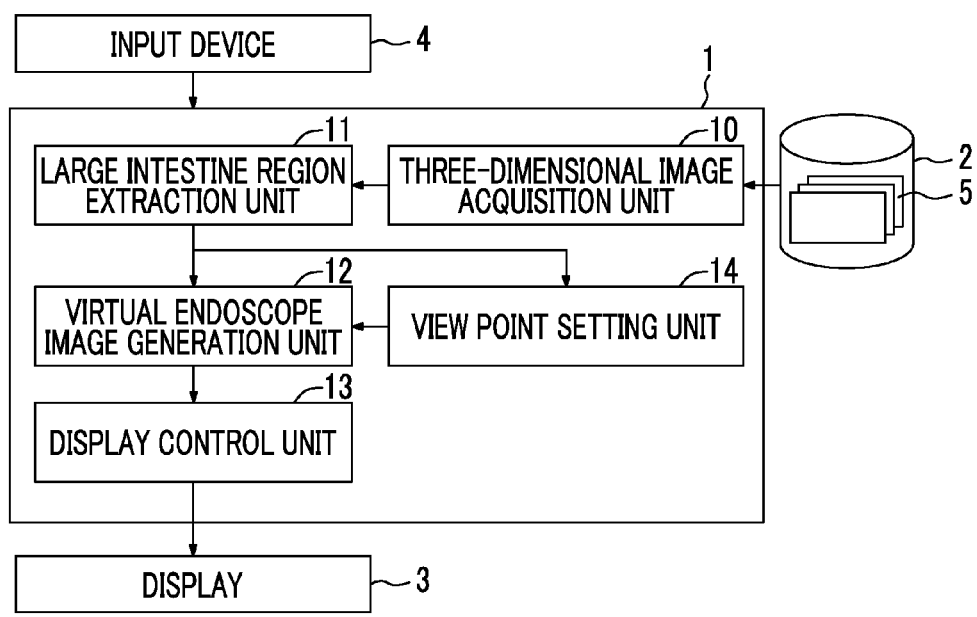
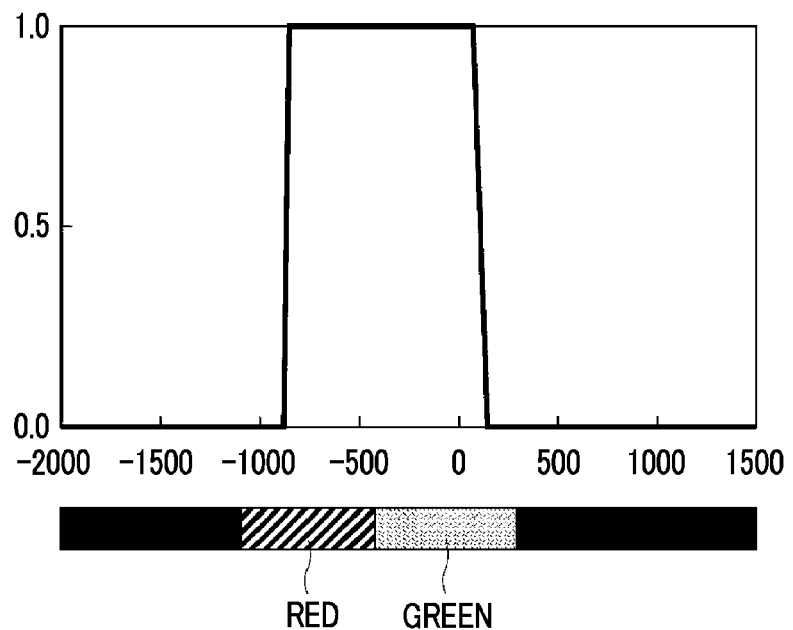

VIRTUAL ENDOSCOPE IMAGE-GENERATING DEVICE, METHOD, AND PROGRAM

CROSS REFERENCE TO RELATED APPLICATIONS

This application is a Continuation of PCT International Application No. PCT/JP2014/003132 filed on Jun. 12, 2014, which claims priority under 35 U.S.C. §119(a) to Japanese Patent Application No. 2013-124350 filed on Jun. 13, 2013. Each of the above applications is hereby expressly incorporated by reference, in its entirety, into the present application.

BACKGROUND OF THE INVENTION

1. Field of the Invention

The present invention relates to a virtual endoscope image-generating device, method, and program for generating a virtual endoscope image representing an inner wall of a large intestine.

2. Description of the Related Art

Recently, extraction of a hollow organ such as a large intestine, a small intestine, or a stomach of a patient from a three-dimensional image captured by a modality such as a computed tomography (CT) device, and use of a three-dimensional image of the extracted hollow organ in image diagnosis has been performed.

For example, CT imaging is performed in a state in which air is in the large intestine, and a three-dimensional image obtained by this photography is subjected to volume-rendering from the inner side of the large intestine. Accordingly, an image as an image when observation is performed using an endoscope can be created, and this image is called a virtual endoscope image.

When this virtual endoscope image is generated, it is necessary to empty the inside of the large intestine before examination, but a residue may remain in the large intestine. When this residue remains in the virtual endoscope image, observation of the inside of the large intestine is disturbed.

Therefore, the residue is imaged in advance in order that CT imaging is performed, and an imaged tagged region is removed through image processing after the CT imaging. Accordingly, a three-dimensional image in which the residue is not virtually present generated, and is subjected to volume rendering. This is called a digital cleansing process. For example, JP2012-504003A and JP2009-511216A disclose a method of detecting polyps or the like after such a digital cleansing process is performed.

SUMMARY OF THE INVENTION

However, when the digital cleansing process is performed on the three-dimensional image of the large intestine region as described above, a tagged region may remain due to a problem of precision of the process and, instead, a shape of folds or polyps of an internal cavity of the large intestine to be observed may be greatly changed.

The present invention has been made in view of the above circumstances, and an object of the present invention is to provide a virtual endoscope image-generating device, method, and program capable of generating a virtual endoscope image in which an inner wall of a large intestine covered by a residue can be observed even without executing a digital cleansing process.

A virtual endoscope image-generating device of the present invention is a virtual endoscope image-generating device including a three-dimensional image acquisition unit that acquires a three-dimensional image including a large intestine region, and a virtual endoscope image generation unit that generates a virtual endoscope image representing an image obtained by virtually imaging the inside of the large intestine region using an endoscope based on the three-dimensional image of the large intestine region, in which the virtual endoscope image generation unit generates the virtual endoscope image based on an opacity template in which a pixel value of the three-dimensional image is associated with an opacity, the opacity template being capable of showing both of an inner wall of the large intestine region and an inner wall of a residue region present in the large intestine region on the virtual endoscope image, a viewpoint set in the vicinity of a boundary between a space region and the residue region in the large intestine region, a set surface set at a position separated by a previously set distance in a previously set line-of-sight direction from the viewpoint, and a pixel value on a light beam vector before the set surface among pixel values of the three-dimensional image on the light beam vector extending from the viewpoint.

Further, the virtual endoscope image-generating device of the present invention may include an opacity change reception unit that receives a change in an opacity setting table.

Further, the set surface may be a flat surface perpendicular to the line-of-sight direction.

Further, the set surface may be a curved surface.

Further, the set surface may include a flat surface and a curved surface perpendicular to the line-of-sight direction.

Further, the curved surface may be a spherical surface or a parabolic curved surface.

Further, the virtual endoscope image-generating device may include a distance change reception unit that receives a change in the distance from the viewpoint.

Further, a viewpoint setting unit that moves a position of the viewpoint along a center line of the large intestine region may be provided, and the viewpoint setting unit may continuously move the viewpoint on the center line to the vicinity of the boundary when the viewpoint on the center line approaches up to a previously set distance from the residue region.

Further, the viewpoint setting unit may continuously move the viewpoint to a position on the center line a previously set distance away from the residue region after the viewpoint is set in the vicinity of the boundary.

Further, a viewpoint setting unit that sets the viewpoint in the vicinity of a center line of the large intestine region may be provided, and the viewpoint setting unit may move the viewpoint from a position in the vicinity of the center line to a position of a pixel value equal to or greater than a threshold value when there is the pixel value equal to or greater than a previously set threshold value on a line extending in a gravity direction from the set viewpoint.

A virtual endoscope image generation method of the present invention is a virtual endoscope image generation method of acquiring a three-dimensional image including a large intestine region, and generating a virtual endoscope image representing an image obtained by virtually imaging the inside of the large intestine region using an endoscope based on the three-dimensional image of the large intestine region, the method including: generating the virtual endoscope image based on an opacity template in which a pixel value of the three-dimensional image is associated with an opacity, the opacity template being capable of showing both of an inner wall of the large intestine region and an inner wall of a residue region present in the large intestine region on the virtual endoscope image, a viewpoint set in the vicinity of a boundary between a space region and the residue region in the large intestine region, a set surface set at a position separated by a previously set distance in a previously set line-of-sight direction from the viewpoint, and a pixel value on a light beam vector before the set surface among pixel values of the three-dimensional image on the light beam vector extending from the viewpoint.

A virtual endoscope image generation program of the present invention is a virtual endoscope image generation program that causes a computer to function as a three-dimensional image acquisition unit that acquires a three-dimensional image including a large intestine region, and a virtual endoscope image generation unit that generates a virtual endoscope image representing an image obtained by virtually imaging the inside of the large intestine region using an endoscope based on the three-dimensional image of the large intestine region, in which the virtual endoscope image generation unit generates the virtual endoscope image based on an opacity template in which a pixel value of the three-dimensional image is associated with an opacity, the opacity template being capable of showing both of an inner wall of the large intestine region and an inner wall of a residue region present in the large intestine region on the virtual endoscope image, a viewpoint set in the vicinity of a boundary between a space region and the residue region in the large intestine region, a set surface set at a position separated by a previously set distance in a previously set line-of-sight direction from the viewpoint, and a pixel value on a light beam vector before the set surface among pixel values of the three-dimensional image on the light beam vector extending from the viewpoint.

According to the virtual endoscope image-generating device, method, and program of the present invention, since the virtual endoscope image is generated based on the opacity template in which a pixel value of the three-dimensional image is associated with an opacity, the opacity template being capable of showing both of the inner wall of the large intestine region and the inner wall of the residue region present in the large intestine region on the virtual endoscope image, the viewpoint set in the vicinity of the boundary between the space region and the residue region in the large intestine region, the set surface set at a position separated by a previously set distance in a previously set line-of-sight direction from the viewpoint, and a pixel value on a light beam vector before the set surface among pixel values of the three-dimensional image on the light beam vector extending from the viewpoint, it is possible to generate a virtual endoscope image in which the inner wall of the large intestine covered by the residue can be observed even without execution of a digital cleansing process. The virtual endoscope image generated according to the present invention will be described below in detail.

BRIEF DESCRIPTION OF THE DRAWINGS

FIG. 1 is a block diagram illustrating a schematic configuration of a medical image diagnosis support system using a virtual endoscope image-generating device, method, and program according to an embodiment of the present invention.

FIG. 2 is a diagram illustrating an example of a color template capable of showing both of an inner wall of a large intestine region and an inner wall of a tagged region present in the large intestine region on a virtual endoscope image.

DESCRIPTION OF THE PREFERRED EMBODIMENTS

Figure 3:
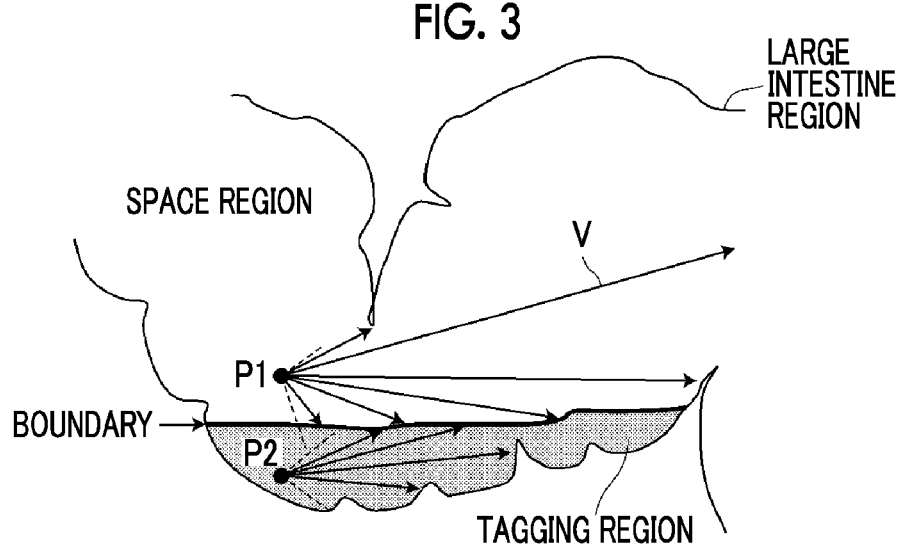
FIG. 3 is a diagram illustrating a virtual endoscope image generated when a viewpoint is set in a space region or the tagged region.

Hereinafter, a medical image diagnosis support system using a virtual endoscope image-generating device, method, and program according to an embodiment of the present invention will be described in detail with reference to the drawings. FIG. 1 is a block diagram illustrating a schematic configuration of a medical image diagnosis support system of this embodiment.

The medical image diagnosis support system of this embodiment includes a medical image display control device 1, a three-dimensional image storage server 2, a display 3, and an input device 4, as illustrated in FIG. 1.

In the medical image display control device 1, a virtual endoscope image generation program of this embodiment is installed on a computer.

The medical image display control device 1 includes a central processing unit (CPU) and a semiconductor memory or a storage device such as a hard disk or a solid state drive (SSD). The virtual endoscope image generation program of this embodiment is installed in the storage device. By this virtual endoscope image generation program being executed by the central processing unit, a three-dimensional image acquisition unit 10, a large intestine region extraction unit 11, a virtual endoscope image generation unit 12, and a viewpoint setting unit 14 as illustrated in FIG. 1 operate.

The three-dimensional image acquisition unit 10 acquires a three-dimensional image 5 of a subject photographed in advance prior to surgery or prior to examination. Examples of the three-dimensional image 5 include volume data reconstructed from sliced data output from a CT device, a magnetic resonance imaging (MRI) device, or the like, and volume data output from a multi slice (MS) CT device or a cone beam CT device. The three-dimensional image 5 is pre-stored together with identification information of the subject in the three-dimensional image storage server 2, and the three-dimensional image acquisition unit 10 is intended to read the three-dimensional image 5 corresponding to the identification information of the subject input by the input device 4 from the three-dimensional image storage server 2. The three-dimensional image acquisition unit 10 may acquire a large number of slice data items to generate volume data. The three-dimensional image acquisition unit 10 in this embodiment acquires the three-dimensional image 5 including the large intestine photographed by the CT device.

The large intestine region extraction unit 11 receives the three-dimensional image 5 acquired by the three-dimensional image acquisition unit 10 and extracts a three-dimensional image of a large intestine region from the input three-dimensional image 5.

In a method of extracting the large intestine region, specifically, a plurality of axial images of a section (axial) perpendicular to a body axis are first generated based on the three-dimensional image 5, and a process of separating an external region of a body and an internal region of the body based on a body surface is performed on the axial image using a known scheme. For example, a binarization process is performed on the input axial image, a contour is extracted through a contour extraction process, and the inside of the extracted contour is extracted as an internal region of the body (human body).

Then, the binarization process using a threshold value is performed on the axial image of the internal region of the body, and a candidate for the large intestine region in each axial image is extracted. Specifically, since air is contained in a tube of the large intestine, a threshold value (for example, −600 or less) corresponding to a CT value of air is set, the binarization process is performed, and an air region in the body of each axial image is extracted as the large intestine region candidate.

Finally, only a portion to which the extracted large intestine region candidate in the body is connected between items of the axial image data is extracted so as to acquire the large intestine region. A method of acquiring the large intestine region is not limited to the above method, and other known methods such as a Region Growing method or a Level Set method may be used.

The virtual endoscope image generation unit 12 generates a virtual endoscope image representing an internal cavity of the large intestine region based on the input three-dimensional image of the large intestine region. The virtual endoscope image is an image obtained by virtually imaging the internal cavity of the large intestine using an endoscope.

Specifically, the virtual endoscope image generation unit 12 generates, as the virtual endoscope image, an image based on central projection obtained by projecting voxel data on a plurality of light beam vectors extending radially about a line-of-sight vector based on a previously set viewpoint and line-of-sight direction on to a predetermined projection surface. As a specific method of the central projection, for example, a known volume rendering scheme or the like may be used.

Here, when the virtual endoscope image is generated in this way, if the digital cleansing process is performed on the three-dimensional image of the large intestine region as described above, the tagged region remains due to a problem of precision of the process and, instead, a shape of folds or polyps of the internal cavity of the large intestine to be observed may be greatly changed.

Therefore, the medical image diagnosis support system of this embodiment generates the virtual endoscope image in which the inner wall of the large intestine covered by the residue can be observed even without execution of the digital cleansing process.

Specifically, in the virtual endoscope image generation unit 12 of this embodiment, a color template (corresponding to an opacity template in claims) as illustrated in FIG. 2 is set in advance. The color template illustrated in FIG. 2 is a color template in which voxel data (pixel value) that is a CT value is associated with an opacity, and can show both of the inner wall of the large intestine region and the inner wall of the tagged region present in the large intestine region on the virtual endoscope image.

The color template illustrated in FIG. 2 assigns the opacity of 1.0 to the voxel data of a boundary portion between a space region in the large intestine and an inner wall of the large intestine, assigns the opacity of 1.0 to the voxel data of a boundary portion between the tagged region and the inner wall of the large intestine, and assigns an opacity of zero to the voxel data in the space region and the voxel data in the tagged region.

More specifically, when the space region is air and a CT value of a contrasting medium of the tagged region is 100 to 200, the CT value of the air is −600 or less, and accordingly, the color template of this embodiment assigns the opacity of zero to voxel data smaller than a first threshold value of −600 or less, assigns the opacity of zero to voxel data greater than a second threshold value of 100 or more, which is the CT value of the contrasting medium, and assigns the opacity of 1.0 to voxel data equal to or greater than the first threshold value or equal to or smaller than the second threshold value. Further, in the color template, colors are set together with opacity. In this embodiment, the inner wall of the large intestine is set to be represented by red, and the inner wall of the tagged region is set to be represented by green. The colors set in the color template are not limited thereto, and other colors may be adopted, or the same color may be assigned to the inner wall of the large intestine and the inner wall of the tagged region.

Further, the first threshold value, the second threshold value, and the color in the color template may be arbitrarily changed by the user. Changes in the first threshold value, the second threshold value, and the color are received by the input device 4, and content after changing is set in the virtual endoscope image generation unit 12. Since the contrasting medium used at the time of imaging the residue has a different CT value depending on a type thereof, the second threshold value can be changed according to the CT value. Types of contrasting medium include Gastrografin (registered trademark), and barium. Further, since for a gas of the space region in the large intestine region, a gas other than air can be used, the first threshold value can be changed according to the CT value of the gas.

Figure 4:
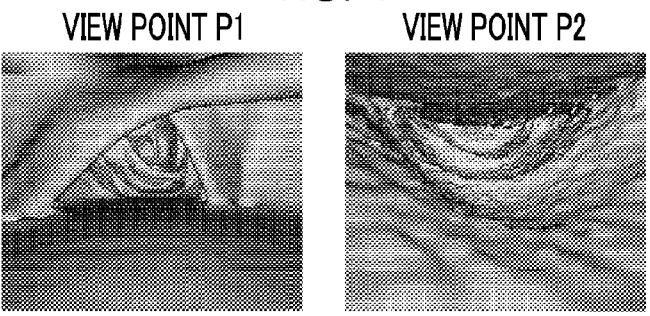
FIG. 4 is a diagram illustrating an example of a virtual endoscope image generated when a viewpoint is set in the space region or the tagged region.

Here, even when the color template as described above is used, if the viewpoint of the virtual endoscope image is set to, for example, a viewpoint P1 as illustrated in FIG. 3 and a virtual endoscope image is generated based on the viewpoint P1 and a light beam vector V, a change in the voxel data when the light beam vector V passes from the space region to the large intestine wall and a change in the voxel data when the light beam vector V passes from the space region to the tagged region boundary cannot be identified, and accordingly, a virtual endoscope image as illustrated in a left diagram of FIG. 4 is obtained. The inside of the large intestine and the inside of the tagged region cannot be simultaneously observed on the virtual endoscope image.

Further, when the viewpoint of the virtual endoscope image is set to a viewpoint P2 illustrated in FIG. 3, and the virtual endoscope image is generated based on the viewpoint P2 and the light beam vector V, a change in the voxel data when the light beam vector V passes from the tagged region to the large intestine wall and a change in the voxel data when the light beam vector V passes from the tagged region to the space region cannot be identified, and accordingly, a virtual endoscope image as illustrated in a right diagram of FIG. 4 is obtained. In this case, the inside of the large intestine and the inside of the tagged region cannot be simultaneously observed on the virtual endoscope image.

Figure 5:
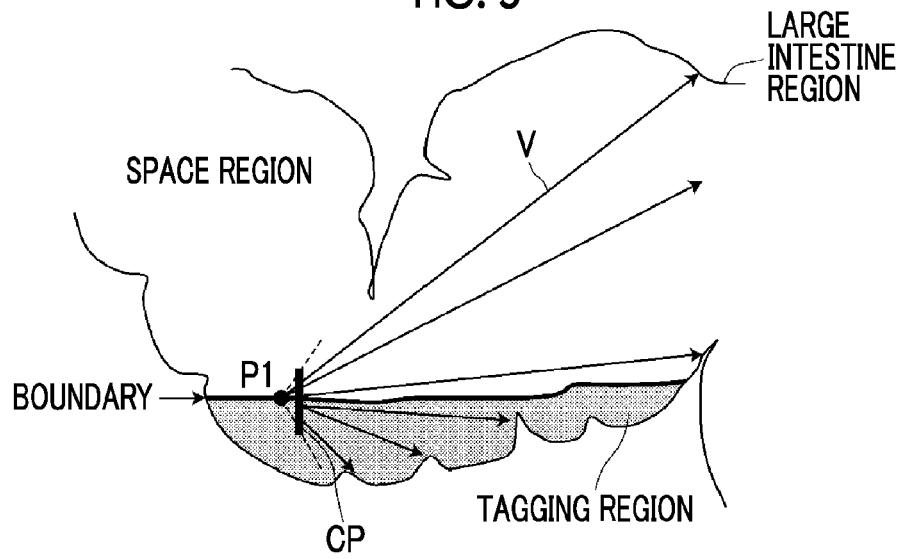
FIG. 5 is a diagram illustrating an example of a viewpoint set in the vicinity of a boundary between the space region and the tagged region, and a clipping plane.

Therefore, when the virtual endoscope image generation unit 12 of this embodiment generates the virtual endoscope image in which both of the internal wall of the large intestine and the inner wall of the tagged region can be observed, the virtual endoscope image generation unit 12 sets the viewpoint of the virtual endoscope image in the vicinity of a boundary between the space region and the tagged region in the large intestine region, as illustrated in FIG. 5. The vicinity of the boundary is, for example, a range of ±5 mm from the boundary. Further, the boundary between the space region and the tagged region may be obtained based on the CT value.

The virtual endoscope image generation unit 12 further sets a clipping plane CP (corresponding to a set surface in claims) at a position separated by a predetermined distance in a line-of-sight direction from the viewpoint set in the vicinity of the boundary, as illustrated in FIG. 5. The line-of-sight direction and the distance from the viewpoint are set in advance, but may be changed by the user. A change in the line-of-sight direction and the distance from the viewpoint is received in the input device 4. It is preferable for the distance between the viewpoint and the clipping plane to be in a range of 3 mm to 30 mm.

Figure 6:
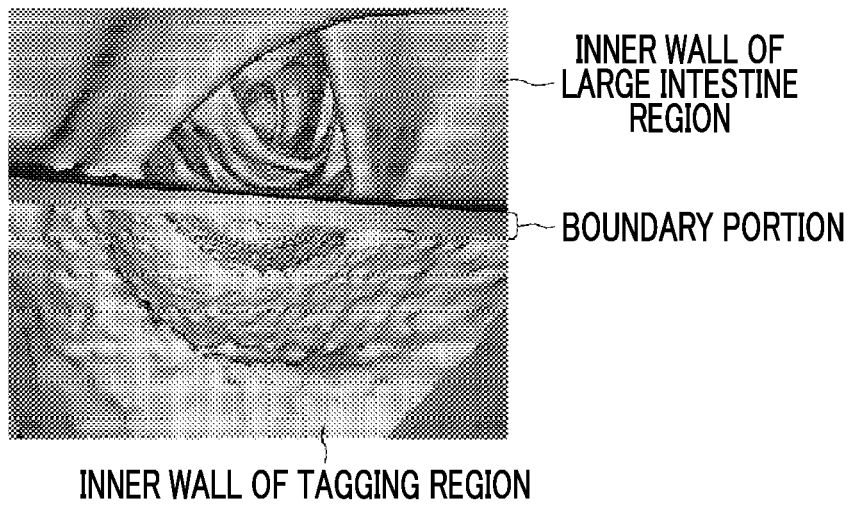
FIG. 6 is a diagram illustrating an example of a virtual endoscope image generated by a virtual endoscope image-generating device, method, and program according to an embodiment of the present invention.

The virtual endoscope image generation unit 12 generates the virtual endoscope image using a volume rendering scheme or the like using the voxel data present on the light beam vector V before the clipping plane CP among items of the voxel data present on the light beam vector V extending radially from the viewpoint, and the above-described color template. FIG. 6 illustrates an example of the virtual endoscope image generated in this manner. As illustrated in FIG. 6, both of the inner wall of the large intestine and the inner walls of the tagged region are shown simultaneously on the virtual endoscope image. Accordingly, a state of the inner wall of the large intestine covered by the residue can also be observed. Further, since the viewpoint is set in the vicinity of the boundary, a boundary surface between the space region and the tagged region shown on the virtual endoscope image illustrated in FIG. 4 is shown on a line in the virtual endoscope image illustrated in FIG. 6, and accordingly, an image of the boundary surface does not obstruct observation.

The viewpoint setting unit 14 sets the viewpoint which is used when the virtual endoscope image generation unit 12 generates the virtual endoscope image. The viewpoint setting unit 14 in this embodiment extracts a center line of the large intestine based on the voxel data of the large intestine, and sequentially switches and sets the viewpoint while moving the viewpoint on a path along the center line. Further, when the viewpoint set on the path approaches the tagged region, the viewpoint setting unit 14 sets the viewpoint in the vicinity of the boundary between the space region and the tagged region in the large intestine region, and then, returns the viewpoint in the vicinity of the boundary to a position of the center line when the point on the center line goes away from the tagged region. A method of moving the viewpoint will be described below in detail.

Further, the viewpoint of the virtual endoscope image is not limited to the setting method as described above. For example, the viewpoint may be set in a three-dimensional image of the large intestine displayed on the display 3 by the user designating an arbitrary point using the input device 4 or may be set by manually designating a predetermined point of the center line of the large intestine.

A display control unit 13 displays the virtual endoscope image generated by the virtual endoscope image generation unit 12 on the display 3.

The input device 4 includes a mouse or a keyboard, and receives an operation input from the user. The input device 4 of this embodiment receives an input for setting the viewpoint or the line-of-sight direction, the first threshold value, the second threshold value, and the color in the color template, the distance between the viewpoint and the clipping plane CP, and the like which are used when the virtual endoscope image is generated as described above. The input device 4 corresponds to an opacity change reception unit and a distance change reception unit in claims.

Figure 7:
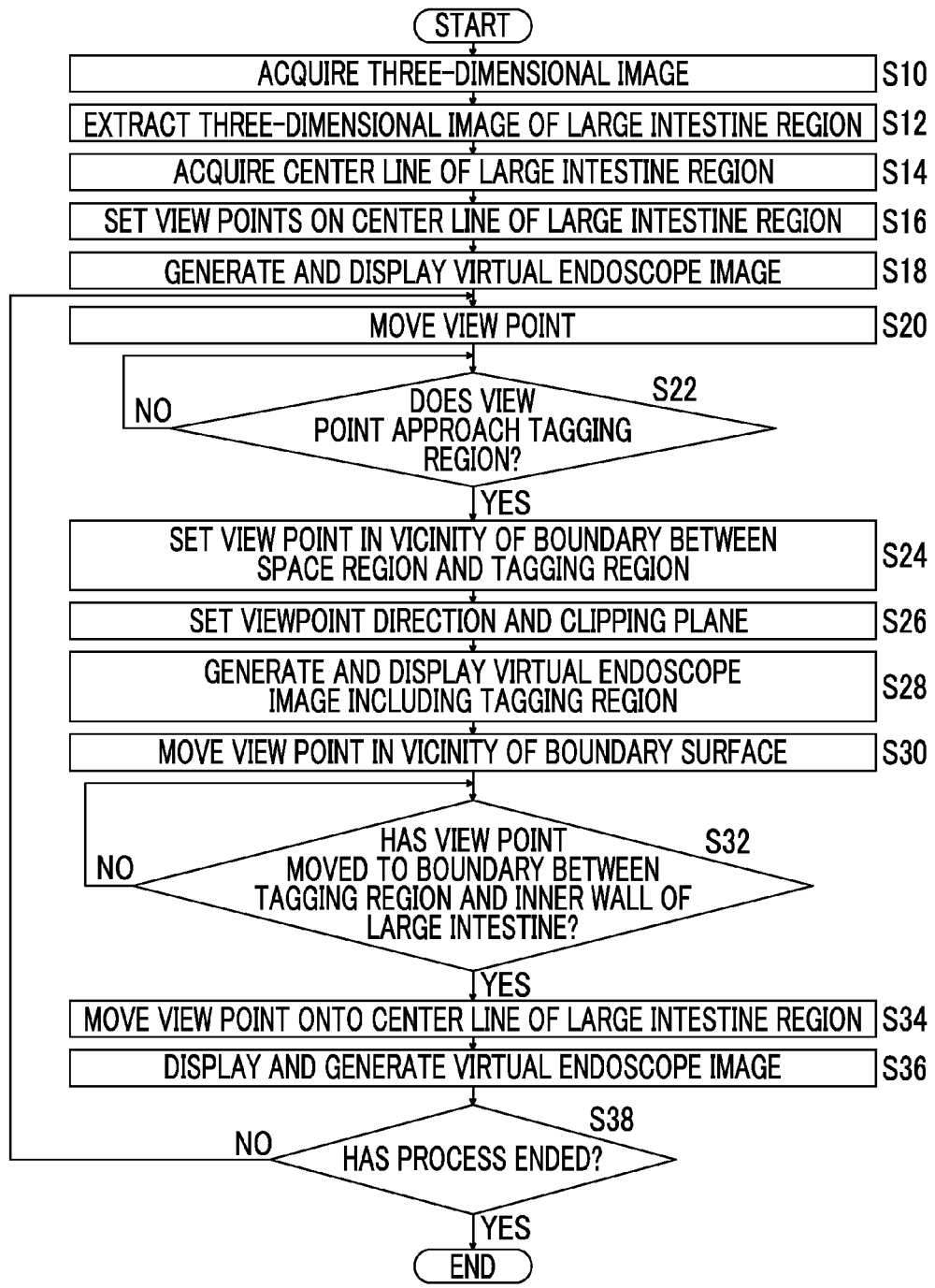
FIG. 7 is a flowchart illustrating an operation of a virtual endoscope image-generating device, method, and program according to an embodiment of the present invention.
Figure 8:
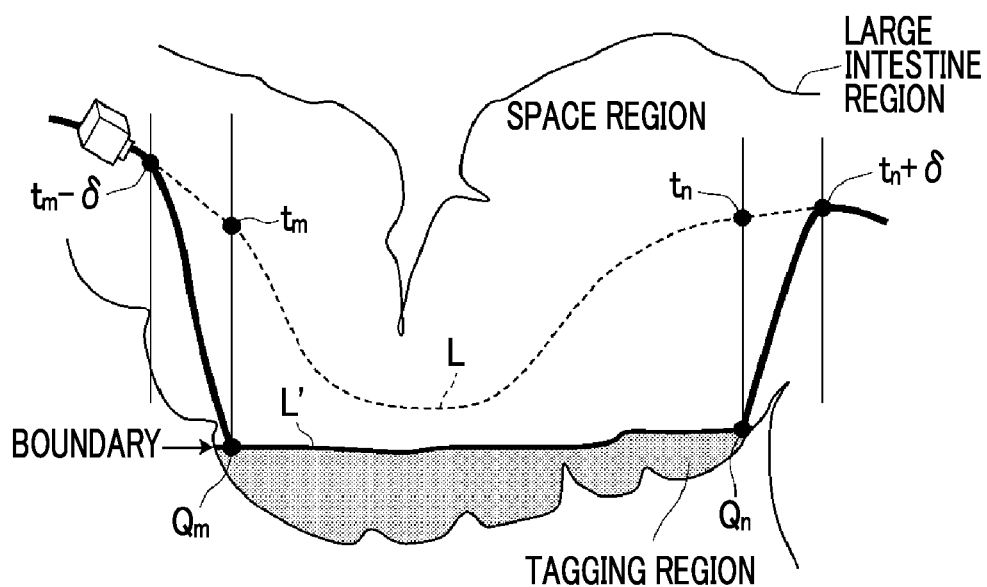
FIG. 8 is a diagram illustrating an example of a viewpoint moving method.

Next, an operation of the medical image diagnosis support system of this embodiment will be described with reference to a flowchart illustrated in FIG. 7, and FIG. 8.

First, identification information of a subject is input by the user using the input device 4, and the three-dimensional image acquisition unit 10 of the medical image display control device 1 reads and acquires the three-dimensional image 5 corresponding to the input identification information of the subject from the three-dimensional image storage server 2 (S10).

The three-dimensional image 5 acquired by the three-dimensional image acquisition unit 10 is input to the large intestine region extraction unit 11, and the large intestine region extraction unit 11 extracts and acquires the three-dimensional image of the large intestine based on the input three-dimensional image 5 (S12).

The three-dimensional image of the large intestine acquired by the large intestine region extraction unit 11 is output to the virtual endoscope image generation unit 12 and the viewpoint setting unit 14, and the viewpoint setting unit 14 acquires the center line of the large intestine region based on the input three-dimensional image of the large intestine (S14), and sets a plurality of viewpoints on the center line (S16).

Among the plurality of viewpoints set by the viewpoint setting unit 14, for example, the first viewpoint in the vicinity of an entrance of the large intestine is input to the virtual endoscope image generation unit 12, and the virtual endoscope image generation unit 12 generates the virtual endoscope image based on the input three-dimensional image of the large intestine, the first viewpoint, the previously set line-of-sight direction, and the above-described color template, and outputs the generated virtual endoscope image to the display control unit 13. The display control unit 13 displays the input virtual endoscope image on the display 3 (S18).

Then, the viewpoint setting unit 14 moves the viewpoint of the virtual endoscope image along the center line of the large intestine region, and sequentially outputs the viewpoints to the virtual endoscope image generation unit 12 (S20). The movement of the viewpoint may be performed automatically or may be performed through setting and inputting in the input device 4 by the user.

The virtual endoscope image generation unit 12 sequentially generates the virtual endoscope images based on the input viewpoints, and outputs the virtual endoscope images to the display control unit 13. The display control unit 13 sequentially switches the input virtual endoscope images and displays the virtual endoscope images on the display 3.

When the viewpoint is moved along the center line of the large intestine region as described above, if the viewpoint after the movement approaches the tagged region, the viewpoint setting unit 14 continuously moves the viewpoint of the virtual endoscope image to the vicinity of the boundary between the space region and the tagged region in the large intestine region and sets the viewpoint (S22: YES, and S24). A method of moving the viewpoint in the viewpoint setting unit 14 in this case will be described in detail below.

Then, the viewpoint setting unit 14 sets the line-of-sight direction and the clipping plane CP (S26), and the virtual endoscope image generation unit 12 generates the virtual endoscope image in which both of the inner wall of the large intestine and the inner wall of the tagged region can be observed, based on the viewpoint set by the viewpoint setting unit 14, the line-of-sight direction, the clipping plane CP, and the color template, and outputs the virtual endoscope image to the display control unit 13. The display control unit 13 displays the input virtual endoscope image on the display 3 (S28).

Subsequently, the viewpoint setting unit 14 moves the viewpoint in a direction in which the large intestine extends in the vicinity of the tagged region boundary (S30). When the viewpoint is moved to the boundary between the tagged region and the inner wall of the large intestine, the viewpoint setting unit 14 continuously moves the viewpoint to the center line of the large intestine region again (S32: YES, and S34).

The virtual endoscope image generation unit 12 generates the virtual endoscope image based on the viewpoint on the center line of the large intestine region again, and outputs the virtual endoscope image to the display control unit 13. The display control unit 13 displays the input virtual endoscope image on the display 3 (S36).

When an instruction to end the process of displaying the virtual endoscope image is not set and input by the user (S38: NO), the process returns to S20 in which the viewpoint is moved along the path on the center line of the large intestine region and set again, and the virtual endoscope image is sequentially generated and displayed based on each viewpoint.

When an instruction to end the process of displaying the virtual endoscope image is set and input by the user (S38: YES), the process ends as it is.

Next, the method of moving the viewpoint in the viewpoint setting unit 14 as described above will be described in detail with reference to FIG. 8.

The viewpoint setting unit 14 first confirms whether or not there is the tagged region on a straight line extending in a gravity direction from the viewpoint at each viewpoint in a viewpoint group on the center line of the large intestine region. Specifically, the viewpoint setting unit 14 confirms whether or not there is voxel data having a CT value equal to or greater than a predetermined threshold value on the straight line extending in the gravity direction described above. A viewpoint at which the tagged region is first confirmed on the straight line extending in the gravity direction is set as a start point $t_m$, and a viewpoint at which the tagged region is last confirmed is set as an end point $t_n$.

The viewpoint setting unit 14 performs correction to a path on which the viewpoint gradually approaches the vicinity of the boundary between the space region and the tagged region between $t_m-\delta$ and $t_m$ when moving the viewpoint along the center line of the large intestine region, and moves the viewpoint along the path. $\delta$ is a previously set fixed value. Further, the path between $t_m-\delta$ and $t_m$ may be a path obtained by connecting a contact point $Q_m$ between a straight line extending in the gravity direction from $t_m$ and the tagged region boundary to $t_m-\delta$ using a straight line or may be a path obtained by connecting the contact point to $t_m-\delta$ using a curved line.

The viewpoint setting unit 14 sets the viewpoint in the vicinity of the boundary between the space region and the tagged region between $t_m$ and $t_n$.

Further, the viewpoint setting unit 14 performs correction to a path on which the viewpoint gradually goes away from the vicinity of the boundary between the space region and the tagged region and approaches the center line of the large intestine region between $t_n$ and $t_n+\delta$, and moves the viewpoint along the path. The path between $t_n$ and $t_n+\delta$ may be a path obtained by connecting a contact point $Q_n$ between a straight line extending in the gravity direction from $t_n$ and the tagged region boundary to $t_n+\delta$ using a straight line or may be a path obtained by connecting the contact point to $t_n+\delta$ using a curved line.

As described above, the viewpoint setting unit 14 corrects a path L along the center line of the large intestine region to a path L' when the viewpoint approaches the tagged region or goes away from the tagged region with the movement of the viewpoint. Accordingly, it is possible to reduce a change in the virtual endoscope image with the movement of the viewpoint, and to achieve being closer to a change in the image in endoscope photography.

Further, in the description of the above embodiment, when the viewpoint of the virtual endoscope image is moved along the path on the center line of the large intestine region, and the viewpoint on the center line approaches up to a previously set distance from the tagged region, the viewpoint on the center line is continuously moved to the vicinity of the boundary of the tagged region, and then, the viewpoint is continuously moved up to the position on the center line a previously set distance away from the tagged region, but a method of moving the viewpoint is not limited thereto.

For example, when the viewpoint setting unit 14 moves the viewpoint along the path on the center line of the large intestine region, the viewpoint setting unit 14 may confirm whether or not there is voxel data equal to or greater than a previously set threshold value on the line extending in the gravity direction from the viewpoint set on the center line of the large intestine region with this movement, and move the viewpoint from the position on the center line to a position of the voxel data equal to or greater than the threshold value when there is voxel data equal to or greater than the threshold value. In this case, it is preferable to move the viewpoint to the position of the voxel data equal to or greater than the threshold value closest to the center line.

Further, an arbitrary position in the vicinity of the center line of the large intestine region may be set as the viewpoint, instead of moving the viewpoint along the path on the center line of the large intestine region as in the above embodiment.

Even when an arbitrary position in the vicinity of the center line of the large intestine region is set as the viewpoint as described above, the viewpoint setting unit 14 may confirm whether or not there is voxel data equal to or greater than a previously set threshold value on the line extending in the gravity direction from the viewpoint set in the vicinity of the center line of the large intestine region, and move the viewpoint from the position of the vicinity of the center line to the position of the voxel data equal to or greater than the threshold value when there is the voxel data equal to or greater than the threshold value. In this case, it is also preferable to move the viewpoint to the position of the voxel data equal to or greater than the threshold value closest to the center line.

When it is confirmed whether or not there is the voxel data equal to or greater than the threshold value on the line extending in the gravity direction from the viewpoint set in the vicinity of the center line of the large intestine region as described above, it is possible to move the viewpoint to the vicinity of the boundary without strictly obtaining the tagged region.

Further, for example, when the tagged region is a relatively small region, if the viewpoint is moved in the vicinity of the boundary, a virtual endoscope image in which observation is difficult may be instead obtained. Therefore, the viewpoint may be moved when the user inputs a predetermined setting in the input device 4, as a timing at which the viewpoint is moved in the vicinity of the boundary.

Figure 9:
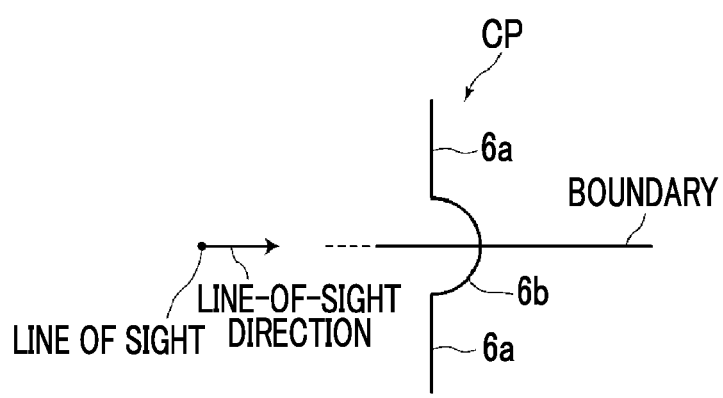
FIG. 9 is a diagram of another example of the clipping plane.

Further, a flat surface perpendicular to the line-of-sight direction is set as the clipping plane CP in the description of the above embodiment, but the clipping plane CP is not limited to a flat surface. The clipping plane CP may be a curved surface, such as a spherical surface or a parabolic curved surface. Further, as illustrated in FIG. 9, the clipping plane CP may include a flat surface 6a and a curved surface 6b, such as a spherical surface or a parabolic curved surface. In this case, the viewpoint is set to be located on the opening side of the curved surface 6b. Further, it is preferable for the boundary between the space region and the tagged region to be set to pass through the curved surface 6b. By forming the clipping plane CP in this way, it is possible to thin the image of the straight line of the boundary portion illustrated in FIG. 6, and to generate a virtual endoscope image in which observation is easy.

What is claimed is:

1. A virtual endoscope image-generating device comprising:
    a three-dimensional image acquisition unit that acquires a three-dimensional image including a large intestine region, and a virtual endoscope image generation unit that generates a virtual endoscope image representing an image obtained by virtually imaging the inside of the large intestine region using an endoscope based on the three-dimensional image of the lame intestine region,
    wherein the virtual endoscope image generation unit generates the virtual endoscope image based on an opacity template in which a pixel value of the three-dimensional image is associated with an opacity, the opacity template being capable of showing both of an inner wall of the large intestine region and an inner wall of a residue region present in the large intestine region on the virtual endoscope image,
    a viewpoint set in the vicinity of a boundary between a space region and the residue region in the large intestine region,
    a set surface set at a position separated by a previously set distance in a previously set line-of-sight direction from the viewpoint, and
    a pixel value on a light beam vector beyond the set surface among pixel values of the three-dimensional image on the light beam vector extending from the viewpoint;
    wherein, in the opacity template, an opacity of a first value is assigned to voxel data of a boundary portion between a space region in the large intestine and the inner wall of the large intestine, an opacity of the first value is assigned to the voxel data of a boundary portion between the residue region and the inner wall of the large intestine, and an opacity of a second value is assigned to the voxel data in the space region and the voxel data in the residue region.

2. The virtual endoscope image-generating device according to claim 1, further comprising:
    an opacity change reception unit that receives a change in the opacity setting template.

3. The virtual endoscope image-generating device according to claim 1,
    wherein the set surface comprises a flat surface perpendicular to the line-of-sight direction.

4. The virtual endoscope image-generating device according to claim 1,
    wherein the set surface comprises a curved surface.

5. The virtual endoscope image-generating device according to claim 4,
    wherein the curved surface comprises a spherical surface or a parabolic curved surface.

6. The virtual endoscope image-generating device according to claim 1,
    wherein the set surface includes a flat surface and a curved surface perpendicular to the line-of-sight direction.

7. The virtual endoscope image-generating device according to claim 1, further comprising:
    a distance change reception unit that receives a change in the distance from the viewpoint.

8. The virtual endoscope image-generating device according to claim 1, further comprising:
    a viewpoint setting unit that moves a position of the viewpoint along a center line of the large intestine region,
    wherein the viewpoint setting unit continuously moves the viewpoint on the center line to the vicinity of the boundary when the viewpoint on the center line approaches up to a previously set distance from the residue region.

9. The virtual endoscope image-generating device according to claim 8,
    wherein the viewpoint setting unit continuously moves the viewpoint to a position on the center line a previously set distance away from the residue region after the viewpoint is set in the vicinity of the boundary.

10. The virtual endoscope image-generating device according claim 1, further comprising:
    a viewpoint setting unit that sets the viewpoint in the vicinity of a center line of the large intestine region,
    wherein the viewpoint setting unit moves the viewpoint from a position in the vicinity of the center line to a position of a pixel value equal to or greater than a threshold value when there is a pixel value equal to or greater than a previously set threshold value on a line extending in a gravity direction from the set viewpoint.

11. The virtual endoscope image-generating device according claim 1, wherein the first value is different than the second value.

12. The virtual endoscope image-generating device according claim 1, wherein the first value is 1.0, and wherein the second value is zero.

13. The virtual endoscope image-generating device according claim 1, wherein, in the color template, colors are set together with a value for opacity.

14. A virtual endoscope image generation method of acquiring a three-dimensional image including a large intestine region, and generating a virtual endoscope image representing an image obtained by virtually imaging the inside of the large intestine region using an endoscope based on the three-dimensional image of the large intestine region, the method comprising:
    generating the virtual endoscope image based on an opacity template in which a pixel value of the three-dimensional image is associated with an opacity, the opacity template being capable of showing both of an inner wall of the large intestine region and an inner wall of a residue region present in the large intestine region on the virtual endoscope image, a viewpoint set in the vicinity of a boundary between a space region and the residue region in the large intestine region, a set surface set at a position separated by a previously set distance in a previously set line-of-sight direction from the viewpoint, and a pixel value on a light beam vector beyond the set surface among pixel values of the three-dimensional image on the light beam vector extending from the viewpoint, wherein, in the opacity template, an opacity of a first value is assigned to voxel wall of the large intestine, an opacity of the first value is assigned to the voxel data of a boundary portion between the residue region and the inner wall of the large intestine, and an opacity of a second value is assigned to the voxel data in the space region and the voxel data in the residue region.

15. A non transitory computer readable recording medium having stored therein a virtual endoscope image generation program that causes a computer to function as a three-dimensional image acquisition unit that acquires a three-dimensional image including a large intestine region, and a virtual endoscope image generation unit that generates a virtual endoscope image representing an image obtained by virtually imaging the inside of the large intestine region using an endoscope based on the three-dimensional image of the lame intestine region, wherein the virtual endoscope image generation unit generates the virtual endoscope image based on an opacity template in which a pixel value of the three-dimensional image is associated with an opacity, the opacity template being capable of showing both of an inner wall of the lame intestine region and an inner wall of a residue region present in the large intestine region on the virtual endoscope image, a viewpoint set in the vicinity of a boundary between a space region and the residue region in the large intestine region, a set surface set at a position separated by a previously set distance in a previously set line-of-sight direction from the viewpoint, and a pixel value on a light beam vector beyond the set surface among pixel values of the three-dimensional image on the light beam vector extending from the viewpoint, wherein, in the opacity template, an opacity of a first value is assigned to voxel data of a boundary portion between a space region in the large intestine and the inner wall of the large intestine, an opacity of the first value is assigned to the voxel data of a boundary portion between the residue region and the inner wall of the large intestine, and an opacity of a second value is assigned to the voxel data in the space region and the voxel data in the residue region.

* * * * *